United States Patent [19] [11] 4,016,260
Karasaki et al. [45] Apr. 5, 1977

[54] NOVEL POLYPEPTIDE PRODUCED BY PSEUDOMONAS

[75] Inventors: Tadashi Karasaki, Toyama; Chikako Hayashi, Koyabe; Etsuko Furuichi, Toyama, all of Japan

[73] Assignee: Toyama Chemical Co., Ltd., Tokyo, Japan

[22] Filed: July 17, 1975

[21] Appl. No.: 596,669

[30] Foreign Application Priority Data

July 22, 1974 Japan .............................. 49-83887
May 22, 1975 Japan .............................. 50-60251

[52] U.S. Cl. ................................ 424/177; 195/96; 260/112 R
[51] Int. Cl.² ................ A61K 35/74; A61K 37/02; C12D 9/20
[58] Field of Search .................. 195/96; 260/112 R; 424/177

[56] References Cited

UNITED STATES PATENTS 3,705,237  12/1972  Grandpierre et al. ............... 195/96

OTHER PUBLICATIONS

Chemical Abstracts, vol. 70, 7646v, (1969).
Chemical Abstracts, vol. 74, 95360g, (1971).
Chemical Abstracts, vol. 75, 4023f, (1971).

Primary Examiner—Alvin E. Tanenholtz
Attorney, Agent, or Firm—Oblon, Fisher, Spivak, McClelland & Maier

[57] ABSTRACT

A novel polypeptide designated as Gamba A having anti-tumor activity, is produced by cultivating a variant strain of Pseudomonas cruciviae, i.e., Pseudomonas sp. No. 2205 (FERM-P 2132 ATCC 31155), and recovering the polypeptide from the cultured broth thereof.

23 Claims, 1 Drawing Figure

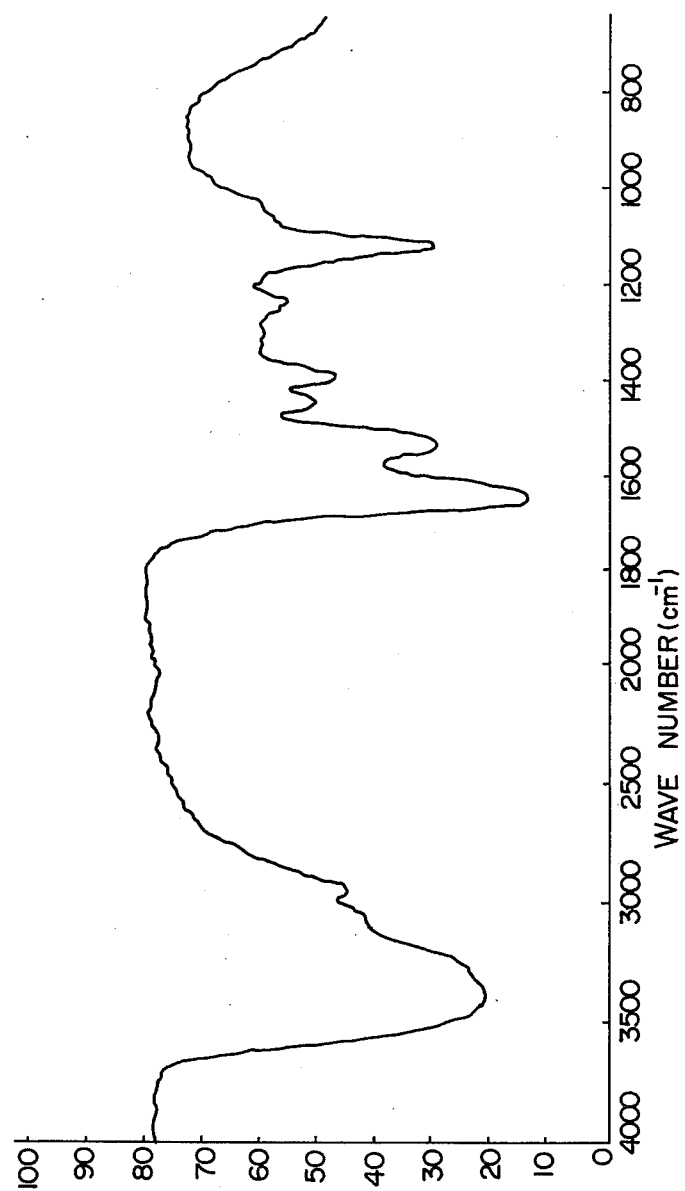
F I G. 1

NOVEL POLYPEPTIDE PRODUCED BY PSEUDOMONAS

This invention relates to a novel polypeptide produced by a microorganism, and to a process for producing the same. More particularly, the invention pertains to a polypeptide having an anti-tumor activity which is produced by a microorganism identified as a variant strain of *pseudomonas cruciviae*, and to a process for producing said polypeptide which comprises culturing the said microorganism and recovering the said polypeptide from the broth.

The cure of tumor diseases is an important subject of the medical science at present, and, as curative medicines therefor, many so-called anti-tumor substances such as synthetic compounds, antibiotics and extracts from various natural materials, possessing an anti-tumor activity, have already been studied and developed and are being clinically used in practice. However, all of them do not show any such prominent curative effects as those of antibiotics against infectious diseases, but some are low in effectiveness while others are high in toxicity. Thus, no satisfactory effects have yet been attained. Accordingly, the advent of excellent curative medicines therefor is generally desired in the medical field.

in order to obtain curative medicines capable of satisfying the above-mentioned desire, the present inventors conducted various investigations and found that a strain belonging to the species Pseudomonas cruciviae, which was newly isolated from soil, produces a polypeptide having a prominent anti-tumor activity and a low toxicity. The polypeptide was designated as "Gamba A" by the present inventors. Based on the above finding, the inventors have accomplished the present invention.

An object of the present invention is to provide a novel polypeptide having an anti-tumor activity.

Another object of the invention is to provide a medicine having a prominent anti-tumor activity and a low toxicity.

A further object of the invention is to provide a process for producing a polypeptide having an anti-tumor activity.

These and other objects and features of this invention will be better understood from the following description taken in connection with the accompanying drawing showing the infra red absorption spectrum of the polypeptide obtained according to this invention.

According to the present invention, a novel polypeptide is produced by culturing aerobically in the presence of nutrient sources a microorganism identified as a variant strain of *Pseudomonas cruciviae* and recovering the resulting polypeptide from the broth.

The variant strain of *Pseudomonas cruciviae* used in the present invention is a strain Pseudomonas sp. No. 2205 (FERM-P 2132, ATCC 31155) which is microorganism isolated by the present inventors from soil collected in Toyama Prefecture, Japan, according to an ordinary plate culture method using a glucose-bouillon neutral agar medium, and has such bacteriological properties as set forth below.

1. Morphological properties:
i. Rods of 1 by 3 to 4 microns in size.
ii. Occurring singly or in pairs, and sometimes in chains.
iii. Motile with polar flagella.
iv. No formation of spores.
v. Extinction temperature 90° C. 5 min.
vi. Gram-negative.
vii. Not acid-fast.

2. Growth state on various media:
i. Broth agar plate culture: Colonies circular convex, smooth, translucent, pale reddish brown.
ii. Broth agar slant culture: Smooth, pale reddish brown, undulate.
iii. Broth liquid culture: Turbid, formation of pellicle with sediment.
iv. Broth gelatin stab culture: Scant growth in layer, no gelatin liquefaction.
v. Litmus milk: Slightly alkaline after 10 days' cultivation. No other change observed.

3. Physiological properties:
i. Nitrates not reduced.
ii. Denitrification reaction: Negative.
iii. Methyl Red test: Negative.
iv. Voges-Proskauer test: Negative.
v. Indole not produced.
vi. Hydrogen sulfide is produced.
vii. Starch not hydrolyzed.
viii. Citric acid utilized.
ix. Inorganic nitrogen sources scarcely utilized.
x. No formation of pigment.
xi. Urease (+)
xii. Oxidase (−)
xiii. Catalase (+)
xiv. Growth ranges: Temperature 20° to 37° C., pH 6.0 to 8.6. Optimum temperature 34° C., optimum pH 6.8 to 7.0.
xv. Aerobic.
xvi. Hugh-Leifson test (O − F test): Negative.
xvii. No acid and gas are produced from any of such saccharides as L-arabinose, D-xylose, D-glucose, D-mannose, D-fructose, D-galactose, maltose, sucrose, lactose, trehalose, D-sorbitol, D-mannitol, inositol, glycerin and starch.

In view of the above-mentioned properties, the present inventors investigated the species of the present strain with reference to Bergey's Manual of Determinative Bacteriology, Seventh Edition. As the result, the present strain coincided substantially with *Pseudomonas cruciviae* (refer to page 114). Accordingly, the inventors compared the present strain with the standard strain *Pseudomonas cruciviae* IFO 12047 deposited in the Institute for Fermentation, Osaka, Japan, by subjecting each strain to shaking culture at 30° C. for 20 hours in a medium prepared by adding 0.2% of each of such organic compounds as shown in Table 1 to a 0.25% aqueous peptone solution, and then adjusting the resulting mixture to pH 7.0. The results obtained are as set forth in Table 1.

Table 1

| | Growth degrees in various media | | | |
| | Present strain | | Ps. cruciviae IFO 12047 | |
| Additive | Growth degree* | pH | Growth degree* | pH |
| --- | --- | --- | --- | --- |
| Sodium acetate | 0.800 | 7.8 | 0.472 | 7.8 |
| Sodium citrate | 0.300 | 7.6 | 1.040 | 8.0 |
| Glucose | 0.081 | 7.2 | 0.249 | 7.4 |
| Glycerin | 0.120 | 7.0 | 0.638 | 7.0 |
| Alginic acid | 0.195 | 7.4 | 0.428 | 7.2 |
| Methylamine | 0.215 | 7.6 | 0.235 | 7.4 |
| Ethanolamine | 0.210 | 7.6 | 0.282 | 7.6 |
| Ethanol | 0.070 | 7.2 | 0.241 | 7.4 |
| Control | 0.062 | 7.4 | 0.356 | 7.4 |

Table 1-continued

| | Growth degrees in various media | | | |
|---|---|---|---|---|
| | Present strain | | Ps. cruciviae IFO 12047 | |
| Additive | Growth degree* | pH | Growth degree* | pH |
| (Non-addition) | | | | |

*The turbidity of the broth was measured by means of a photoelectric colorimeter having a 610 mµ filter and a 1 cm cell, and was represented by the asbsorbance thereof.

As is clear from Table 1, the present strain was extremely low in growth degree in the control medium, i.e. the basal medium incorporated with no organic compound, but showed a marked increase in growth degree in the medium incorporated with any of sodium acetate, sodium citrate, alginic acid, methylamine and ethanolamine, and could utilize these organic compounds. In contrast to this, Ps. cruciviae IFO 12047 showed proper growth even in the control medium, and the increase in growth degree thereof was observed only in the cases where sodium citrate and glycerin were used, indicating that the said strain could utilize only said two compounds among those mentioned above. Thus, a clear difference in utilizability of organic compounds is observed between the present strain and Pseudomonas cruciviae.

From the above, the inventors denominated that present strain as Pseudomonas sp. No. 2205, recognizing it as a variant of Pseudomonas cruciviae, and deposited the strain on August 28, 1973 in the Fermentation Research Institute, Agency of Industrial Science and Technology, Chiba, Japan, and on May 27, 1975 in the American Type Culture collection, 12301 Parklawn Drive Rockville Md. 20852, United States, to obtain the deposition numbers of FERM-P 2132 and ATCC 31155, respectively.

The present invention is explained in detail below with respect to each of the steps for cultivation of Pseudomonas sp. No. 2205 (FERM-P 2132, ATCC 31155), the recovering steps which may be divided into the step for extraction of Gamba A from the broth and the step for purification of the extract.

1. Cultivation step:

The medium is most preferably a bouillon medium containing meat extract and peptone, but may be any of natural medium components used for general bacteria cultivation such as soybean infusion, meat or organ infusion, corn steep liquor, yeast extract, malt extract, potato infusion, casein hydrolyzate or mixture thereof. It is also preferable to add thereto a growth-promoting agent such as acetic or citric acid, ethylamine, ethanolamine or alginic acid. The initial pH of the medium is preferably from 6.0 to 8.6, more preferably from 6.8 to 7.0, and the cultivation temperature is preferably from 20° to 37° C., more preferably from 30° to 32° C. The cultivation is carried out aerobically according to any of stationary culture (for 10 to 20 days), shaking culture (for 16 to 24 hours), and submerged culture, i.e. tank culture, (for 24 to 36 hours), whereby Gamba A is produced.

2. Extraction step:

The polypeptide of the present invention exists in both the cells and the culture filtrate, and can be recovered according to an ordinary procedure adopted in the recovery of polypeptides. Thus, the polypeptide of the present invention is recovered by separating the polypeptide and proteins from a solution containing them which has been obtained by filtering the broth or extracting the cells contained in the filtrate thus obtained, and separating the polypeptide from proteins.

i. Extraction from culture filtrate:

The cells are freed from the solution by centrifugation or filtration to obtain a culture filtrate. To this culture filtrate is added 0.1 to 5% by weight of active carbon based on the weight of the culture filtrate, and the resulting mixture is allowed to stand or stirred at a temperature of below 40° C. for 1 to 40 hours, whereby Gamba A is adsorbed on the active carbon. The pH to be adopted in this case is preferably from 4 to 9, more preferably from neutral to slightly alkaline. The active carbon is recovered by filtration or centrifugation and then suspended in water, acidic water (pH 2.0 to 6.0) or alkaline water (pH 8.0 to 12.0), or in such solvent as methanol, ethanol or 30 to 90% (V/V) acetone-water, and the resulting suspension is stirred or shaken at 5° to 40° C. for 1 to 6 hours, whereby the Gamba A dissolves out into the water or the solvent. Subsequently, the active carbon is separated by filtration, and the filtrate is concentrated under reduced pressure at a temperature of below 45° C. to obtain an extract of the Gamba A. As the adsorbent, there may be used, besides the above-mentioned active carbon, any natural or synthetic adsorbent suitable for the later-mentioned chamical properties of Gamba A.

Alternatively, to the culture filtrate is added a protein precipitant such as tannic or picric acid, without using the adsorbent, whereby Gamba A precipitates together with proteins contained. This precipitate is dissolved in alkaline water or an aqueous alkaline solvent to obtain an extract of the Gamba A.

ii. Extraction from cells:

The solution is subjected to centrifugation or filtration to collect the cells. The collected cells are suspended in water, acidic water (pH 2.0 to 6.0) or alkaline water (pH 8.0 to 12.0), or in such a solvent as methanol, ethanol or 30 – 90% (V/V) acetone-water, and the resulting suspension is allowed to stand at 5° to 40° C. for 2 to 48 hours, whereby Gamba A dissolves out into the water or the solvent. This liquid is freed from insolubles by centrifugation or filtration and concentrated under reduced pressure at a temperature of below 45° C., and then ethanol is added thereto to a concentration of 70% to deposit precipitate. The precipitate is removed, and the supernatant is concentrated in the same manner as above to obtain an extract of the Gamba A.

Alternatively, the collected cells are suspended in a small amount of water, and the resulting cell suspension is subjected to supersonic treatment, freeze-melting treatment or other suitable mechanical cell-rupture treatment. To the resulting ruptured cell suspension, ethanol is added to a concentration of 80% to deposit precipitate. The precipitate is removed, and the supernatant is concentrated under reduced pressure to obtain an extract of Gamba A.

iii. Purification step:

The extract obtained in the above is subjected, either as it is or after removal of an organic solvent if this is contained, to salting-out treatment which is an ordinary protein precipitation method, whereby Gamba A comes to be present chiefly in the supernatant formed by the salting-out treatment. The deposited proteins are separated by filtration, and the filtrate is subjected to dialysis treatment or charged with a water-miscible solvent to remove inorganic salts, and is further washed with n-butanol or treated with a cation or anion exchange-resin to remove amino acids. The thus purified extract is concentrated under reduced pressure at a temperature of below 45° C. To the concentrate, methanol, ethanol, n-butanol or acetone is added to a concentration of 90% or more to deposit yellow to reddish yellow precipitate. The precipitate is recovered by filtration, further purified by dialysis if necessary, and then dried, whereby the desired polypeptide, Gamba A is obtained.

Physicochemical and biological properties of the thus obtained Gamba A are as described below.

(1) Physicochemical properties:
a. A polypeptide.
b. Melting point: 206° C. (decomp.).
c. Specific rotation: $[\alpha]D$ 27 $-54°$ (concentration 0.35 in water).
d. Ultraviolet absorption spectrum shows no specific absorption.
e. Infrared absorption spectrum: Absorptions observed at 2.95, 3.40, 6.05, 6.55, 6.95 7.20, 8.15 and 9.00 $\mu$ as shown in the accompanying drawing.
f. Solubility in solvents: Easily soluble in water; soluble in methanol and ethanol; sparingly soluble in butanol; and insoluble in acetone, benzene, chloroform, ethyl acetate, pyridine, dioxane and dimethylformamide.
g. Biuret reaction: positive; Ninhydrin reaction: negative; Orcinol reaction: negative; Ferric chloride reaction: negative; Sakaguchi's reaction: positive; Silver nitrate reaction: negative;
h. An acidic substance.
i. A white to pale yellow granular powder.
j. Consitutive amino acids: A hydrolyzate obtained by treating the present substance with N-HC1 under reflux for 24 hours was identified according to thin layer chromatography to confirm that at least alginine and threonine were present as constitutive amino acids.
k. Since the present substance is a high molecular weight compound, no significant elementary analysis values and molecular weight (according to freezing point depression method) thereof can be measured by usual test methods.

(2) Biological properties:
i. Anti-tumor activity:

Into the peritonea of mice (ddys strain, male, 20 ± 1 g., 5 weeks old, 5 mice per group) were inoculated ten million Ehrlich's ascites tumor cells per mouse. One hour after the inoculation, such dose as shown in Table 2 of Gamba A was intraperitoneally administered to the mice. Thereafter, the same dose of Gamba A was administered two times at intervals of one day. Thus, the administration was effected 3 times in total. During 3 months from the inoculation day, the mice were fed and observed to obtain such results as shown in Table 2. As is clear from Table 2, there was obtained such marked effect that all the mice could survive by 3 times' administration of Gamba A in a dose of 20 mg/kg per time.

Table 2

| Dose mg/kg/time | Anti-tumor activity test Dead mice | | Effectiveness | |
|---|---|---|---|---|
| | Mortality | Average* survival days | Survival** mice | Effectiveness ratio |
| 20 | 0/5 | — | 5/5 | 100% |

Table 2-continued

| Dose mg/kg/time | Anti-tumor activity test Dead mice | | Effectiveness | |
|---|---|---|---|---|
| | Mortality | Average* survival days | Survival** mice | Effectiveness ratio |
| 10 | 3/5 | 29.0 | 2/5 | 40% |
| 5 | 4/5 | 28.2 | 1/5 | 20% |
| Control (non-administration) | 5/5 | 26.4 | 0/5 | 0% |

*Calculated only in the case of dead mice.
**After recogniton of their normal growth, the survival mice were killed after 3 months.

ii. Toxicity:

Gamba A was intraperitoneally administered in such doses as shown in Table 3 to mice (ddys strain, male, 20 ± 1 g.). After 3 days, the mice were observed to show such results as set forth in Table 3. As is clear from Table 3, $LD_{50}$ of Gamba A is more than 400 mg/kg.

Table 3

| Toxicity (intra-peritoneal administration) | |
|---|---|
| Dose mg/kg | Mortality |
| 400 | 1/5 |
| 200 | 0/5 |
| 100 | 0/5 |
| 50 | 0/5 | iii. Antimicrobial activity:

Gamba A was subjected to antimicrobial activity test using *E. coli* NIHJ, *S. aureus FDA* 209 and *B. subtilis* ATCC 6633 as test microorganisms. The results of the test showed that it had no antimicrobial activity against any of the test microorganisms, when the test microorganisms were inoculated and cultured in a neutral bouillon medium containing 80 mcg/ml of Gamba A at a temperature of 37° C for 20 hours.

The results shown in Table 3 indicate that Gamba A displays accurate anti-tumor activity even when administered in a dose of less than 1/20 of its $LD_{50}$ value. Further, many anti-tumor substances additionally have antimicrobial activity and hence are so-called cytotoxins, whereas Gamba A has no antimicrobial activity, and therefore it is sufficiently inferable from this respect that Gamba A is less in toxicity.

The present invention is illustrated in more detail below with reference to examples, in which % represents the proportion (g) of solute per 100 cc. of solution.

EXAMPLE 1

300 Milliliters of a medium (pH 7.0) containing 1% of meat extract and 1% of peptone was charged into a 500 ml-Erlenmeyer flask. In this medium, Pseudomonas sp. No. 2205 was subjected to aerobical stationary culture at 28° C. for 15 days. As a result, the broth became turbid, formed a film and then settled, and the pH reached 8.4. 24 Liters of this broth was centrifuged at 20,000G for 10 minutes to separate the broth into the culture filtrate and the cells.

i. Extraction from culture filtrate:

To the culture filtrate was added 30 g. of active carbon, and the resulting mixture was stirred at room temperature for 60 minutes and then subjected to filtration to recover the active carbon. This active carbon was suspended in a mixed solvent comprising 50 ml. of water, 240 ml. of ethanol and 1.5 ml. of acetic acid, and the resulting suspension was shaken at room temperature for 120 minutes to elute Gamba A. After separating the active carbon by filtration, the eluate was concentrated under reduced pressure at a temperature below 45° C. to a volume of 50 ml. In the thus concentrated eluate, about 35 g. of ammonium sulfate was dissolved to form a saturated solution, which was then allowed to stand at 5° C. for 120 minutes to deposit proteins contained therein. The deposited proteins were separated by filtration, and the filtrate was diluted with water to 5 times the original volume, adjusted to a pH of 7.0 to 7.4 by addition of sodium hydroxide, and then charged with 500 g. of active carbon. The resulting mixture was stirred at room temperature for 60 minutes, and then subjected to filtration to recover the active carbon. The recovered active carbon was washed with 40 ml. of n-butanol, and then suspended in 60 ml. of 95% ethanol. The resulting suspension was stirred at room temperature for 20 minutes to elute Gamba A, and then subjected to filtration to divide the suspension into the eluate (a) and the active carbon (b).

Eluate (a):

The eluate (a) was concentrated under reduced pressure at a temperature below 45° C. to form about 10 ml. of an aqueous solution. This solution was charged into a cellophane bag, and dialyzed for 180 minutes against distilled water. Subsequently, the liquid inside the bag was concentrated under reduced pressure at a temperature below 45° C. to a volume of 0.3 ml., and then 2.7 ml. of ethanol was added thereto to deposit yellow precipitate. The deposited precipitate was collected by centrifugation, dissolved in 0.2 ml. of water, and then charged with 1.8 ml. of ethanol to deposit Gamba A in the form of pale yellow granules. The deposition was completed at 5° C., and the granules were collected by centrifugation, washed with acetone and then dried by means of a vacuum desiccator to obtain 4 mg. of a pale yellow powder of the Gamba A.

Active carbon (b):

The active carbon (b) was suspended in a mixed solvent comprising 20 ml. of water, 80 ml. of ethanol and 0.5 ml. of acetic acid, and the resulting suspension was stirred at room temperature for 120 minutes to elute Gamba A. After separating the active carbon by filtration, the eluate was concentrated under reduced pressure to form about 10 ml. of an aqueous solution. This solution was charged into a cellophane bag, and dialyzed for 180 minutes against distilled water to remove the acetic acid. Subsequently, the liquid inside the bag was concentrated under reduced pressure at a temperature below 45° C. to a volume of 3 ml., and then 7 ml. of ethanol was added thereto to deposit reddish brown precipitate. The deposited precipitate was removed by centrifugation, and the supernatant was concentrated under reduced pressure to a volume of 0.5 ml. and then charged with 3.5 ml. of ethanol to deposit yellow precipitate. The deposited precipitate was collected by centrifugation, dissolved in 0.2 ml. of water, and then charged with 1.8 ml. of ethanol to deposit Gamba A in the form of yellow granules. The deposition was completed at 5° C., and the granules were collected by centrifugation, washed with acetone and then dried by means of a vacuum desiccator to obtain 17 mg. of a yellow powder of the Gamba A.

(ii) Extraction from cells:

The cells were suspended in 500 ml of water, and the resulting suspension was subjected to supersonic rupture treatment for 10 minutes using an supersonic wave generator with a frequency of 9,000 cycles and an oscillator output of 180 watts. To the thus treated suspension, acetic acid was added to a concentration of 0.5%, and the resulting mixture was centrifuged at 20,000G for 10 minutes. To the supernatant was added 1/10 the amount thereof of Amberlite IR-4B. The resulting mixture was shaken at room temperature for 30 minutes to remove the acetic acid, and the Amberlite IR-4B was separated by filtration. The filtrate was concentrated under reduced pressure at a temperature below 45° C. to about 1/20 of the original volume. To the concentrate, ethanol was added to a concentration of 70% to deposit precipitate. The deposited precipitate was removed by centrifugation, and the supernatant was concentrated under reduced pressure to remove the ethanol and then charged with water to make 50 ml. The thus formed liquid was subjected to the same ammonium sulfate salting-out and active carbon adsorption of the salted-out liquid as in the case of the aforesaid culture filtrate. Subsequently, the active carbon was subjected to elution using 50 ml. of the same mixed ethanol solvent as mentioned previously, and then the same treatment as in the aforesaid item (b) was effected to obtain 20 mg. of a pale yellow granular powder of Gamba A.

In short, a total of 41 mg. of the pure Gamba A powder i.e. 21 mg. from the culture filtrate and 20 mg. from the cells, was obtained by use of 24 liters of the broth. All of the powder products had same properties as previously described.

EXAMPLE 2

5 Liters of the same medium as in Example 1 was charged into a 10 liter-jar fermentor. In this medium, Pseudomonas sp. No. 2205 was subjected to tank culture at 30° C. for 24 hours with stirring at 400 r.p.m. while introducing air in a proportion of 6 liters per minute, whereby the growth of the microorganism reached maximum and the pH of the broth reached 9.0. From this broth, Gamba A was extracted in the same manner as in Example 1 to obtain a total of 4.5 mg. of a pale yellow pure Gamba A powder, i.e. 2 mg. from the culture filtrate and 2.5 mg. from the cells. The Gamba A powder product had the same properties as previously described.

What is claimed is:

1. A process for producing the novel polypeptide Gamba A which comprises aerobically culturing in the presence of nutrient sources the variant strain of Pseudomonas cruciviae which is Pseudomonas sp. No. 2205 (FERM-P 2132, ATCC 3115) and recovering the resulting Gamba A polypeptide from the broth having the following physicochemical properties:

a. A polypeptide
b. Melting point: 206° C (decomp.)
c. Specific rotation: D 27 −54° (concentration 0.3% in water)
d. Ultraviolet absorption spectrum shows no specific absorption Infrared absorption spectrum: Absorptions observed at 2.95, 3.40, 6.05, 6.55, 6.95, 7.20, 8.15 and 9.00$\mu$ as shown in FIG. 1 f. Solubility in solvents: Easily soluble in water; soluble in methanol and ethanol; sparingly soluble in butanol; and insoluble in acetone, benzene, chloroform, ethyl acetate, pyridine, dioxane and dimethylformamide g. Biuret reaction: positive, Ninhydrin reaction: negative, Orcinol reaction: negative, Ferric chloride reaction: negative, Sakaguchi's reaction: positive,- Silver nitrate reaction: negative h. An acidic substance i. A white to pale yellow granular powder j. Constitutive amino acids: A hydrolyzate obtained by treating the present substance with N-HCl under reflux for 24 hours was identified according to thin layer chromatography to confirm that at least alginine and threonine were present as constitutive amino acids k. Since the present substance is a high molecular weight compound, no significant elementary analysis values and molecular weight (according to freezing point depression method) thereof can be measured by usual test methods.

2. A process according to claim 1, wherein the nutrient source is a member selected from the group consisting of bouillon, peptone, soybean infusion, meat extract, meat or organ infusion, corn steep liquor, yeast extract, malt extract, potato infusion, casein hydrolyzate, and mixtures thereof.

3. A process according to claim 2, wherein the nutrient source is a mixture of meat extract and peptone.

4. A process according to claim 1, wherein the nutrient source contains a growth-promoting agent selected from the group consisting of sodium acetate, sodium citrate, alginic acid, methylamine and ethanolamine.

5. A process according to claim 1, wherein the pH of the medium at the beginning of the cultivation is 6.0 to 8.6.

6. A process according to claim 5, wherein the pH of the medium at the beginning of the cultivation is 6.8 to 7.0.

7. A process according to claim 1, wherein the cultivation is carried out at 20° to 37° C.

8. A process according to claim 7, wherein the cultivation is carried out at 30° to 32° C.

9. A process according to claim 1, wherein the recovery of the polypeptide is carried out from both of the culture filtrate and cells.

10. A process according to claim 1, wherein the recovery of the polypeptide is carried out by separating the polypeptide and proteins from a solution containing them which has been obtained by filtering the broth or extracting the cells contained in the filtrate thus obtained, and separating the polypeptide from proteins.

11. A process according to claim 10, wherein the separation of the polypeptide and proteins is carried out by subjecting the aqueous solution to adsorption.

12. A process according to claim 11, wherein the adsorbent is active carbon.

13. A process according to claim 10, wherein the separation of the polypeptide and proteins is carried out by precipitating them with a precipitating agent.

14. A process according to claim 13, wherein the precipitating agent is selected from the group consisting of water-miscible alcohols, picric acid and tannic acid.

15. A process according to claim 10, wherein the separation of the polypeptide and proteins is carried out by salting out the proteins.

16. A process according to claim 10, wherein the solution containing the polypeptide and proteins is the filtrate of the broth.

17. A process according to claim 10, wherein the solution containing the polypeptide and proteins is an extract of cells of the broth.

18. A process according to claim 17, wherein the extract of cells is obtained by immersing the collected cells in water, acidic water or alkaline water to extract the polypeptide.

19. A process according to claim 17, wherein the extract of cells is obtained by immersing the collected cells in methanol, ethanol or aqueous acetone to extract the polypeptide.

20. A process according to claim 17, wherein the extract of cells is obtained by suspending the collected cells in a small amount of water, subjecting the cell suspension to supersonic treatment and then extracting the polypeptide from the ruptured cell suspension.

21. A process according to claim 17, wherein the extract of cells is obtained by suspending the collected cells in a small amount of water, subjecting the suspension to freeze-melting treatment and then extracting the polypeptide from the ruptured cell suspension.

22. The Gamba A polypeptide produced by the process according to claim 1.

23. A composition comprising the Gamba A polypeptide of claim 22 and a pharmaceutically acceptable adjuvant.

* * * * *